United States Patent [19]

Kabeta et al.

[11] Patent Number: 4,927,949

[45] Date of Patent: May 22, 1990

[54] METHOD OF PREPARING AN AMINOALKYLALKOXYSILANE

[75] Inventors: Keiji Kabeta; Michio Zenbayashi, both of Gunma, Japan

[73] Assignee: Toshiba Shilicone Co., Ltd., Tokyo, Japan

[21] Appl. No.: 406,728

[22] Filed: Sep. 13, 1989

[30] Foreign Application Priority Data

Sep. 30, 1988 [JP] Japan ................. 63-246097

[51] Int. Cl.$^5$ ................................ C07F 7/10
[52] U.S. Cl. ..................................... 556/413
[58] Field of Search ........................... 556/413

[56] References Cited

U.S. PATENT DOCUMENTS 3,470,225  9/1969  Kriorre et al. .............. 556/413
3,864,373  2/1975  Seiler et al. ................ 556/413
4,481,364  11/1984  Chew et al. ................ 556/413
4,556,722  12/1985  Zeirk et al. ................ 556/413

FOREIGN PATENT DOCUMENTS 0284447  9/1988  European Pat. Off. ........... 556/413

Primary Examiner—Paul F. Shaver
Attorney, Agent, or Firm—Flynn, Thiel, Boutell & Tanis

[57] ABSTRACT

An improved method of preparing an aminoalkylalkoxy silane of the formula:

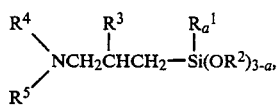

in which $R^1$ and $R^2$ independently are alkyl groups having 1–8 carbon atoms, $R^3$ is a hydrogen atom or an alkyl group having 1–6 carbon atoms, $R^4$ and $R^5$ independently are a member selected from the group consisting of a hydrogen atom, an alkyl group having 1–10 carbon atoms, $-CH_2CH_2NH_2$, $-CH_2CH_2NHCH_2CH_2NH_2$, an allyl group, a substituted phenyl group and a nonsubstituted phenyl group and a is an integer from 0–2, comprises the step of reacting a silane compound with an allylamine in the presence of a catalyst composition selected from the group consisting of (1) a rhodium complex catalyst and a heterocyclic compound containing nitrogen and/or sulfur atoms and (2) a rhodium complex catalyst having a heterocyclic compound containing nitrogen and/or sulfur atoms as a ligand.

4 Claims, No Drawings

METHOD OF PREPARING AN AMINOALKYLALKOXYSILANE

FIELD OF THE INVENTION

This invention relates to a new method of preparing an aminoalkylalkoxysilane. In particular, this invention relates to the hydrosilylation of an allylamine (including N-substituted allylamine) with an alkoxyhydrosilane in the presence of a rhodium complex catalyst having a heterocyclic compound containing nitrogen and/or sulfur atoms as a ligand.

PRIOR ART

The contact catalytic addition of an allylamine to an alkoxyhydrosilane is a widely known method of preparing an aminoalkylalkoxysilane. From among the more commonly known catalysts, platinum catalysts are generally known as being the most useful for these reactions. However, these reactions with the platinum catalyst produces both $\gamma$ and $\beta$-isomers of the final product at, for example, an isomer ratio of $\gamma:\beta$ isomers of approximately 15:1 being reported (Pat. Disclosure SHO 60-81189). Since the $\gamma$-isomer is the desired isomer, a comparatively pure product (95% or more) of the $\gamma$-isomer can only be obtained by removing the $\beta$-isomer. For this reason, it is desirable to utilize a hydrosilylation reaction method which effectively increases the ratio of either the $\gamma$ or $\beta$-isomer in the final product.

In addition, it is described in Pat. Disclosure SHO 61-229885 that the ratio of $\gamma$-isomer to $\beta$-isomer can be increased to 95% or more by using a method which utilizes a rhodium-triorganophosphorous complex catalyst. However, the activity of the rhodium complex, which has a triorganophosphorous ligand, is comparatively low with respect to hydrosilylation reactions, and is disadvantageous in terms of industrial utilization due to the reaction requiring a long period of time.

In addition, reaction catalysts such as rhodium hydride carbonyl-tris(triphenylphosphine), rhodium hydridetetrabis(triphenylphosphine), and rhodium carbonyl triphenylphosphine acetylacetate are disadvantageous in terms of industrial utilization due to the complexity of their formulation.

OBJECT OF THE INVENTION

The object of the present invention is to provide a method which improves the yield of the reaction product, aminoalkylalkoxysilane, and also increases the ratio of $\gamma:\beta$ isomers in an addition reaction of an allylamine with an alkoxyhydrosilane.

SUMMARY OF THE INVENTION

As a result of earnest studies directed to such a method, the inventors were able to complete the present invention by discovering that the above object could be accomplished by using a rhodium complex which has a heterocyclic compound containing nitrogen and/or sulfur atoms as a ligand as the catalyst.

DESCRIPTION OF THE PREFERRED EMBODIMENT

In other words, the present invention relates to a method of preparing an aminoalkylalkoxysilane of the formula:

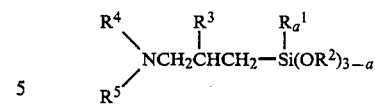

in which $R^1$ and $R^2$ independently are alkyl groups having 1-8 carbon atoms, $R^3$ is a hydrogen atom or an alkyl group having 1-6 carbons, $R^4$ and $R^5$ independently are a group selected from among a hydrogen atom, an alkyl group having 1-10 carbons, $-CH_2CH_2NH_2$, $-CH_2CH_2NHCH_2CH_2NH_2$, an allyl group and a substituted or nonsubstituted phenyl group, and a is an integer from 0-2, which is prepared by reacting a silane compound of the formula: $R_a^1HSi(OR^2)_{3-a}$ in which $R^1$, $R^2$ and a are as described previously) with an allylamine of the formula:

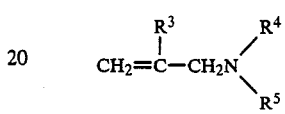

(in which $R^3$, $R^4$ and $R^5$ are as described previously) in the presence of (a) a heterocyclic compound containing nitrogen and/or sulfur atoms and a rhodium complex catalyst, or (b) a rhodium complex catalyst having a heterocyclic compound containing nitrogen and/or sulfur atoms as a ligand.

The silane compound used in this invention is of the formula: $R_a^1HSi(OR^2)_{3-a}$ (in which $R^1$, $R^2$ and a are as described previously), and contains a hydrogen atom, which is bonded to a silicon atom, and an alkoxy group. Although $R^1$ and $R^2$ are independently alkyl groups having 1-8 carbon atoms, they are typically either methyl or ethyl groups. Examples of such a silane compound include triethoxysilane, trimethoxysilane, tripropoxysilane, triisopropoxysilane, tributoxysilane, methyldimethoxysilane, ethyldimethoxysilane, methyldiethoxysilane, dimethylmethoxysilane, trioctyloxysilane, methyldioctyloxysilane and dimethyloctyloxysilane.

The allylamine used in this invention is of the formula:

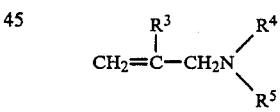

(in which $R^3$, $R^4$ and $R^5$ are as described previously) and is another starting substance which forms an aminoalkylalkoxysilane by a hydrosilylation reaction with the previously described silane compound. Examples of such an allylamine include allylamine, N,N-dimethylallylamine, N,N-diethylallylamine, N-allylamine, methallylamine, diallylamine, triallylamine, allylethylenediamine, N-phenylallylamine and allyldiethylenetriamine.

In the method of this invention, the effective ratio of the silane compound to the allylamine can be changed within a range of 1.5:1-1:1.5, and is preferably 1.1:1-1:1.1.

An improvement of the present invention is the combined use of a rhodium complex and a heterocyclic compound containing nitrogen and/or sulfur atoms, or the use of a rhodium complex having a heterocyclic compound containing nitrogen and/or sulfur atoms as a ligand, as the catalyst in a hydrosilylation reaction between a silane compound and an allylamine.

This rhodium-based catalyst may be either prepared in advance prior to hydrosilylation, or formed in the system immediately prior to the hydrosilylation reaction. In terms of ease in conducting the reaction, it is more preferable that the desired complex be formed in the system.

It is preferable that the source of rhodium that is used at the time of preparing the catalyst have a ligand which is easily replaced by a complex ring containing nitrogen and/or sulfur atoms. Phosphine ligands, which are ligands of comparatively strong coordination strength, cannot be used in this case. Examples of suitable complexes include bis(norbornadiene)rhodium(I)tetrafluoroborate, bis(1,5-cyclooctadiene)rhodium(I)tetrafluoroborate, bis(norbornadiene)rhodium(I)perchlorate, di-$\mu$-cholorobis(norbornadiene)dirhodium(I), and di-$\mu$-chlorotetra(ethylene)dirhodium(I).

In addition, examples of the heterocyclic compound which contains nitrogen and/or sulfur atoms that is used as a ligand include phenothiazine, benzotriazole, N,N-dimethylaminopyridine, quinoline, morpholine and 2,2'-dipyridyl.

Preparation of the catalyst should be carried out with an allylamine derivative, the raw material of the reaction. A catalyst necessary for the reaction can be obtained by mixing the previously described complex, which serves as the source of rhodium, and a heterocyclic compound containing nitrogen and/or sulfur atoms, which is used as a ligand, with the allylamine derivative.

The mixing ratio of the rhodium complex used as the raw material and the nitrogen and/or sulfur-containing heterocyclic compound used as the ligand should be 1:2 (mole ratio) or more and more preferably, 1:5 or more.

Although the concentration of the rhodium used in the method of this invention depends on the reaction temperature and reaction time, in general, the concentration of rhodium should be approximately 5ppm or more, based on the total weight of all of the silane and amine that is used. The upper limit of catalyst concentration is not firmly set and should be determined primarily by commercial and economic factors. Preferably, the catalyst should contain rhodium in a range of approximately 10-200 ppm based on the total amount of silane and amine used and more preferably, approximately 30-100 ppm.

Although the hydrosilylation reaction can be carried out at a temperature range of $-30°$ to $180°$ C., it is normally carried out at a more preferable range of $50°-150°$ C. The reaction is normally carried out at atmospheric pressure. However, the reaction pressure may be increased or decreased as necessary.

In addition, although the use of a solvent at the time of reaction is not particularly required, one may be used in order to increase the solubility of the catalyst or to help control the reaction temperature. Examples of such a solvent include hydrocarbon-type solvents such as toluene, xylene, cyclohexane, n-hexane, n-heptane, naphtha, mineral spirit or petroleum benzine, halogenated hydrocarbon-type solvents such as chloroform, carbon tetrachloride, trichloroethylene, perchloroethylene and 1,1,1-trichloroethane, ether-type solvents such as ethyl ether, tetrahydrofuran, and ethylene glycol diethyl ether, ester-type solvents such as ethyl acetate, butyl acetate and amyl acetate, ketone-type solvents such as acetone, methyl ethyl ketone, and methyl isobutyl ketone, as well as aprotic polar solvents such as dimethylformamide and dimethylacetoamide.

Since the reaction time varies according to the raw material used, catalyst or solvent, and reaction temperature, etc., it is not subject to any particular limitation. However, conditions are normally set so that the reaction is completed in 0.5-3 hours. The reaction is carried out by normal methods.

The aminoalkylalkoxysilane that is obtained with the method of the present invention is useful as, for example, a glass-plastic cement, an auxiliary bonding agent, an additive for phenol-based bonding agents/blocking material (foundry) mixtures, a vinyl plastisol, a polyurethane elastomer, as well as a adhesion promoter for epoxy and acryl-based inks. Examples of these aminoalkylalkoxysilanes include aminopropyltrimethoxysilane, aminopropyltriethoxysilane, aminopropylmethyldimethoxysilane, aminopropyltriisopropoxysilane, N-phenylaminopropyltriethoxysilane, N-phenylaminopropylmethyldiethoxysilane, tris(triethoxysilylpropyl)amine, bis(triethoxysilylpropyl)amine, tris(trimethoxysilylpropyl)amine, bis(trimethoxysilylpropyl)amine, and N-($\beta$-aminoethyl)aminopropyltriethoxysilane.

According to this invention, it is possible to industrially prepare an aminopropylalkoxysilane at a high yield having a $\gamma:\beta$ isomer ratio of 24:1 using a rhodium complex of a heterocyclic compound containing nitrogen and/or sulfur atoms.

The following provides a detailed description of the method of this invention using examples. Furthermore, the term "parts" in the examples refers to parts by weight.

EXAMPLE 1

571 parts of allylamine, 0.38 part of [Rh(NBD)$_2$]$^{(+)}$.BF$_4^{(-)}$ (note: NBD: Norbornadiene), 1.0 part of phenothiazine and 1640 parts of triethoxysilane were charged into a sealed tube and allowed to react in an oil bath for 2 hours at 130° C. Following cooling, the product was analyzed with gas chromatography. Aminopropyltriethoxysilane was produced at a yield of 65% and moreover, the ratio of $\gamma:\beta$ isomer was 24:1.

COMPARATIVE EXAMPLE 1

Except for omitting the addition of phenothiazine, the reaction was carried out using the same method as that of Example 1. When the product was analyzed with gas chromatography, the yield was 55% and the ratio of $\gamma:\beta$ isomer was 4:1.

COMPARATIVE EXAMPLE 2

Using 0.93 part of RhCl(PPH$_3$)$_3$ (note: PPH$_3$: Triphenylphosphine) as the catalyst, the reaction was carried out in the same manner as Example 1 with the exception of not using [Rh(NBD)$_2$]$^{(+)}$.BF$_4^{(-)}$ and phenothiazine. When the product was analyzed with gas chromatography, it was found that the yield was 25% and 70% or more of the raw materials triethoxysilane and allylamine remained unreacted. The ratio of the $\gamma:\beta$ isomers of aminopropyltriethoxysilane was 10:1.

EXAMPLE 2

With the exception of the addition of 0.25 part of Rh$_2$Cl$_2$(C$_6$H$_{12}$)$_2$ instead of [Rh(NBD)$_2$]$^{(+)}$.BF$_4^{(-)}$, the reaction was carried out in the same manner as Example 1. When the product was analyzed with gas chromatography, the target compound was obtained with a yield of 60% and a $\gamma:\beta$ isomer ratio of 23:1.

EXAMPLE 3

With the exception of the addition of 0.60 part of benzotriazole instead of phenothiazine, the reaction was carried out in the same manner as Example 1. As a result of analysis by gas chromatography, the target compound was obtained with a yield of 60% and a $\gamma:\beta$ isomer ratio of 20:1.

EXAMPLE 4

With the exception of the addition of 1340 parts of methyldiethoxysilane instead of triethoxysilane, the reaction was carried out in the same manner as Example 1. As a result of analysis by gas chromatography, aminopropylmethyldiethoxysilane was obtained at a yield of 65% and a $\gamma:\beta$ isomer ratio of 24:1.

What is claimed is:

1. A method of preparing an aminoalkylalkoxysilane of the formula:

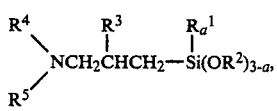

in which $R^1$ and $R^2$ independently are alkyl groups having 1-8 carbon atoms, $R^3$ is a hydrogen atom or an alkyl group having 1-6 carbon atoms, $R^4$ and $R^5$ independently are a member selected from the group consisting of a hydrogen atom, an alkyl group having 1-10 carbon atoms, $-CH_2CH_2NH_2$, $-CH_2CH_2NHCH_2CH_2NH_2$, an allyl group, a substituted phenyl group and a nonsubstituted phenyl group and a is an integer from 0-2, comprising the step of reacting an alkoxysilane of the formula:

$$R_a^1HSi(OR^2)_{3-a},$$

where $R^1$, $R^2$ and a are described above, with an allylamine of the formula:

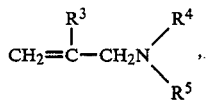

where $R^3$, $R^4$ and $R^5$ are as described above, in the presence of a catalyst composition selected from the group consisting of (1) a rhodium complex catalyst and a heterocyclic compound containing nitrogen and/or sulfur atoms and (2) a rhodium complex catalyst having a heterocyclic compound containing nitrogen and/or sulfur atoms as a ligand.

2. The method of claim 1, wherein said catalyst composition is a rhodium complex catalyst having a heterocyclic compound containing nitrogen and/or sulfur atoms as a ligand.

3. The method of claim 2, wherein said catalyst composition is formed in-situ, during the preparation of the aminoalkylalkoxysilane.

4. The method of claim 1, wherein said catalyst composition is a rhodium complex catalyst and a heterocyclic compound containing nitrogen and/or sulfur atoms.

* * * * *